United States Patent
Nogues et al.

(10) Patent No.: US 11,066,528 B2
(45) Date of Patent: Jul. 20, 2021

(54) PRODUCTION OF POLYAMIDE POWDERS BY ESTER AMINOLYSIS

(71) Applicant: Arkema France, Colombes (FR)

(72) Inventors: Pierre Nogues, Bernay (FR); Geoffroy Cammage, Rouen (FR)

(73) Assignee: ARKEMA FRANCE, Colombes (FR)

( * ) Notice: Subject to any disclaimer, the term of this patent is extended or adjusted under 35 U.S.C. 154(b) by 57 days.

(21) Appl. No.: 15/539,002

(22) PCT Filed: Dec. 22, 2015

(86) PCT No.: PCT/FR2015/053706
§ 371 (c)(1),
(2) Date: Jun. 22, 2017

(87) PCT Pub. No.: WO2016/102879
PCT Pub. Date: Jun. 30, 2016

(65) Prior Publication Data
US 2017/0349714 A1 Dec. 7, 2017

(30) Foreign Application Priority Data

Dec. 22, 2014 (FR) ...................................... 1463132

(51) Int. Cl.
| | | |
|---|---|---|
| *C08J 3/14* | (2006.01) | |
| *C08G 69/28* | (2006.01) | |
| *C08G 69/04* | (2006.01) | |
| *C08G 69/26* | (2006.01) | |
| *C08G 69/02* | (2006.01) | |
| *A61K 8/02* | (2006.01) | |
| *A61K 8/88* | (2006.01) | |
| *A61Q 19/00* | (2006.01) | |

(52) U.S. Cl.
CPC ................. *C08J 3/14* (2013.01); *A61K 8/022* (2013.01); *A61K 8/88* (2013.01); *A61Q 19/00* (2013.01); *C08G 69/02* (2013.01); *C08G 69/04* (2013.01); *C08G 69/26* (2013.01); *C08G 69/28* (2013.01); *A61K 2800/10* (2013.01); *A61K 2800/412* (2013.01); *C08J 2377/06* (2013.01)

(58) Field of Classification Search
None
See application file for complete search history.

(56) References Cited

U.S. PATENT DOCUMENTS

| | | | | |
|---|---|---|---|---|
| 3,011,904 A | * | 12/1961 | Pickett | ..................... C08J 3/226 427/196 |
| 3,329,653 A | | 7/1967 | Bavers et al. | |
| 3,376,260 A | | 4/1968 | Gerhard | |
| 3,379,695 A | * | 4/1968 | Wolfes | ................... C08G 69/26 528/336 |
| 3,459,714 A | | 8/1969 | Wolfes et al. | |
| 3,465,059 A | * | 9/1969 | Seven | ................... C08G 69/00 525/183 |
| 5,093,466 A | | 3/1992 | Patton et al. | |
| 6,127,513 A | * | 10/2000 | Ohara | ................... C08G 69/04 528/310 |
| 2009/0072424 A1 | | 3/2009 | Herve et al. | |
| 2009/0075081 A1 | * | 3/2009 | Ouvrard | ..................... C08J 3/12 428/402 |
| 2014/0205783 A1 | * | 7/2014 | Jeol | ........................ C08G 69/00 428/36.9 |

FOREIGN PATENT DOCUMENTS

| | | |
|---|---|---|
| EP | 0 515 553 A1 | 12/1992 |
| EP | 1 797 141 A1 | 6/2007 |
| WO | WO 91/13113 A1 | 9/1991 |
| WO | WO 2006/040443 A1 | 4/2006 |
| WO | WO 2008/005415 A1 | 1/2008 |

OTHER PUBLICATIONS

International Search Report (PCT/ISA/210) dated Mar. 14, 2016, by the French Patent Office as the International Searching Authority for International Application No. PCT/FR2015/053706.
Written Opinion (PCT/ISA/237) dated Mar. 14, 2016, by the French Patent Office as the International Searching Authority for International Application No. PCT/FR2015/053706.

* cited by examiner

*Primary Examiner* — Susan T Tran
*Assistant Examiner* — William Craigo
(74) *Attorney, Agent, or Firm* — Buchanan Ingersoll & Rooney P.C.

(57) ABSTRACT

A method for producing a polycondensate powder dispersion, characterised in that it includes at least one step of polycondensation: i) of at least one diester and at least one diamine, and/or ii) at least one amino ester, while stirring, in a solvent that can solubilise both the diamine and the diester and/or the amino ester but not the polyamide that forms during the polycondensation, at a temperature between 30° C. and the boiling temperature of the solvent, in order to produce a powder precipitate dispersed in the solvent.

8 Claims, No Drawings

PRODUCTION OF POLYAMIDE POWDERS BY ESTER AMINOLYSIS

FIELD OF THE INVENTION

The present invention relates to the processes for synthesizing polyamide (PA) powders from at least one diester and at least one diamine and/or from at least one amino ester. The present invention relates more particularly to a process for producing polyamide powders by polycondensation. It also relates to the polyamide that can be obtained by means of the process of the invention, either in the form of a powder dispersion or in the form of a free powder, and to the use thereof.

TECHNICAL BACKGROUND

Industrially, polyamides are prepared by polymerization, either of at least one diamine and diacid pair, or of at least one amino acid, or of a mixture of these two types of monomers. These polyamides are used when they are in powder form, for specific applications such as surface coatings, cosmetics and powder agglomeration techniques by electromagnetic radiation-induced melting or sintering for producing objects.

Patent document WO 2008/005415 describes a process for synthesizing high-molecular-weight polyamide. This synthesis consists of a polymerization in an extruder, at a very high temperature of at least 300° C., between monomers of diamine and diacid type, or even diester type, although this technique is not verified by examples in the case of the diester.

Patent document EP 0 515 553 describes a resin made up of polyoxamides and copoly(amide-oxamide), synthesized by polycondensation in the presence of di-n-butyl oxalate. The polymerization is carried out in two successive steps: in a first step, a prepolymerization is carried out in toluene, at ambient temperature, so as to form a white precipitate, and then the toluene is evaporated off. In a second step, the polymerization continues at a temperature of 270° C. The macromolecular and oxygen-permeability properties of these polyoxamides and copoly(amide-oxamide)s are described, but no mention is made of the characteristics of the white precipitate obtained.

A problem noted in the context of the synthesis of polyamides from ester is that of the side reactions which promote in particular the appearance of N-alkylated amines. These unwanted products disrupt the polycondensation and also the crystallization of the polyamides.

It is also necessary to mention various processes for producing polyamide powders known to those skilled in the art. Most of these processes comprise two steps, with the polymerization being carried out in a first step and the formation of the particles, for example by milling, being carried out in a second step.

Polyamide powders can be obtained for example by milling or cryomilling of granules of polyamide having an initial mean diameter of about 3 mm. Nevertheless, these mechanical transformations by size reduction often result in particles of irregular shape, having a wide particle size distribution and the mean diameter of which is rarely less than 100 µm.

It is also known practice to prepare polyamide powders by dissolution in and then reprecipitation from a "good solvent" for the polyamide. Since the solvents for polyamides at ambient temperature are very corrosive, the choice of the "good solvent" often involves an alcohol which dissolves the polyamide at high temperature, which means that the work must be carried out under pressure. The facilities must hold the pressure and the safety conditions are strict.

Document EP 1 797 141 describes a technique for obtaining thermoplastic polymer powder by means of a process of alloying with a lost matrix. The incompatible blending of two polymers, in the molten state, results in the formation of nodules of one polymer in the other. The thermoplastic polymer powders are then recovered by dissolving the water-soluble matrix in water. This process, carried out in several steps, is thus of limited industrial interest.

Finally, it is known practice to obtain powders of polymer such as polyamide by anionic precipitation polymerization of lactams in solution. The polymerization is carried out in the presence of the monomers, of a solvent for the monomers, of an initiator, of a catalyst and of an activator and with stirring at a temperature in the region of 100° C. This process is specific to polyamides and poly(ester-amide)s obtained from monomers of lactam and lactone type. According to this process, it is possible to obtain powders of micrometric size and of spheroidal shape. However, it is not very flexible and allows only a slight diversification of the nature of the powders according to the desired final properties of the powder, by varying the nature of the monomers, for example.

There is thus a need to develop an improved process for producing polyamide powder, which can in particular be adapted to a wider range of monomers, including those which are ester-based, while at the same time preserving the fine control of the shape of the particles obtained.

SUMMARY OF THE INVENTION

The invention relates firstly to a process for producing a polycondensate powder dispersion, characterized in that it comprises at least one step of polycondensation:
 i) of at least one diester and at least one diamine,
 and/or
 ii) of at least one amino ester,
with stirring, in a solvent that can dissolve both the diamine and the diester and/or the amino ester, but not the polyamide which forms during the polycondensation, at a temperature included in the range of 30° C. to the boiling point of said solvent, such that a powder precipitate dispersed in the solvent is obtained.

According to one advantageous embodiment of the invention, said process for producing powder also comprises a step of separation of the solvent and of recovery of the powder.

Advantageously, the process of the invention is carried out in the optional presence of a polycondensation catalyst, the content of which is included in the range of from 0 to 50 mol %, preferably from 0.01 mol % to 50 mol %, preferably from 0.01 mol % to 30 mol %, preferably from 0.01 mol % to 20 mol %, relative to the number of moles of all of the reagents. The term "all of the reagents" is intended to mean the diamine.diester and/or amino ester pair. The addition of catalyst above 30 mol %, or even already above 20 mol %, generally has no more notable effect on the reaction yield; a yield "ceiling" is then observed.

Advantageously in the invention, said at least one diester is of formula $R_1-(CH_2)_m-R_2$, wherein m represents an integer ranging from 0 to 36, and $R_1$ and $R_2$ represent identical or different ester functions of general formula $COOR_3$, wherein $R_3$ represents a saturated or unsaturated, linear or branched alkyl chain of from 1 to 5 carbon atoms and/or of formula $R_1-(C_6H_4)-R_2$, wherein n represents an integer ranging from 1 to 2, and $R_1$ and $R_2$ represent identical or different ester functions of general formula $COOR_3$, wherein $R_3$ represents a saturated or unsaturated, linear or branched alkyl chain of from 1 to 5 carbon atoms.

According to one advantageous embodiment of the invention, said at least one diester is chosen from methyl oxalate, ethyl oxalate, propyl oxalate, butyl oxalate, dibutyl adipate, dibutyl azelate, dimethyl sebacate, dibutyl suberate, dibutyl isophthalate, dibutyl sebacate, dibutyl laurate, and mixtures thereof.

Advantageously, said at least one diamine is chosen from aliphatic diamines having from 6 to 12 carbon atoms, said diamine possibly being a saturated aryl and/or cyclic diamine.

Advantageously, said diamine is chosen from ethylenediamine, hexamethylenediamine, piperazine, tetramethylenediamine, octamethylenediamine, 1,9-diaminononane, decamethylenediamine, dodecamethylenediamine, 1,5-diaminohexane, 2,2,4-trimethyl-1,6-diaminohexane, polyol diamines, isophorone diamine (IPD), methyl pentamethylene diamine (MPDM), bis(aminocyclohexyl)methane (BACM), bis(3-methyl-4-aminocyclohexyl)methane (BMACM), meta-xylylenediamine, bis-p-aminocyclohexylmethane and trimethylhexamethylenediamine, and mixtures thereof.

Advantageously, said at least one amino ester is of formula $R_5$—$(CH_2)_p$—$R_6$, with p representing an integer ranging from 0 to 36, $R_5$ being a primary or secondary amine function and $R_6$ being an ester function of general formula $COOR_7$, $R_7$ being a saturated or unsaturated, linear or branched alkyl chain of from 1 to 5 carbon atoms.

Advantageously, said polycondensation catalyst is chosen from sodium hydride, potassium hydride, sodium, sodium stearate, ortho-phosphoric acid, stearic acid, ethanol, phenol, sodium methoxide, sodium ethoxide, and mixtures thereof.

Advantageously, said solvent is chosen from linear alkanes, cycloaliphatic alkanes, halogenated solvents and mixtures thereof, the solvent preferably having a boiling point above the polymerization temperature included in the range of from 30° C. to 180° C., preferably in the range of from 30° C. to 150° C., preferably from 30 to 100° C., and preferably in the region of 100° C. Furthermore, it is preferred to use one (or more) solvent(s) that is (are) liquid at ambient temperature (temperature included in the range of from 15 to 25° C.).

Advantageously, said polycondensation is characterized by a simultaneous precipitation in the form of powders of the polycondensate.

Advantageously, said stirring is at a speed included in the range of from 1 to 2000 rpm, preferably carried out by means of a paddle stirring system, even more preferentially by means of a paddle and counter-paddle stirring system.

The invention also relates to a polyamide that can be obtained according to the process described above.

Advantageously, said polycondensate powder comprises particles of free powder which have a spheroidal shape, a D50 measured according to ISO standard 13320-1:1999 included in the range of from 1 to 200 μm, and which comprise traces of ester chain ends, preferably 10 to 4000 meq/kg of ester chain ends, relative to the weight of polycondensate.

Advantageously, the polycondensate comprises at least one monomer chosen from the units: 2.9, 2.10, 4.6, 4.T, 6, 6.6, 6.9, 6.10, 6.12, 6.T, 9.2, 10.2, 10.10, 10.12, 10.T, 11, 12, 12.9, 12.10, 12.12, 12.T, and mixtures thereof having alternating or block units. In this embodiment, T is terephthalic acid.

Advantageously, the powder exhibits traces of the solvent used for the dispersion, preferably from 10 to 10 000 ppm of solvent Advantageously, traces of a polycondensation catalyst are found, preferably from 0 to 50 mol %, preferably from 0.01 mol % to 30 mol %, preferably from 0.01 mol % to 20 mol %, relative to the number of moles of polycondensate.

Advantageously, traces of monoalcohol, preferably from 0.01% to 5% by weight, relative to the total weight of the powder, of alcohol of formula $R_3OH$ and/or $R_7OH$, wherein $R_3$ and $R_7$ each represent a saturated or unsaturated, linear or branched alkyl chain of from 1 to 5 carbon atoms, are found.

Advantageously, said polycondensate is an oligomer of number-average molar mass included in the range of from 300 g/mol to 5000 g/mol.

Advantageously, said polycondensate is a polyamide of number-average molar mass of between 5000 and 30 000 g/mol, preferably included in the range of from 8000 to 15 000 g/mol.

Advantageously, the polyamide powder is used in coatings, paints, anticorrosion compositions, paper additives, powder agglomeration techniques by electromagnetic radiation-induced melting or sintering for producing objects, electrophoresis gels, multilayer composite materials, the packaging, toy, textile, automobile and/or electronics industry, and in cosmetic, pharmaceutical or perfumery products.

Advantageously, said oligomer powder is used as an ester and/or amine reactive synthon in polymer chain extension reactions, either alone or as an additive in powder agglomeration techniques by electromagnetic radiation-induced melting or sintering for producing objects, as a polyamide reinforcement or as an organic filler for composite materials.

The invention also relates to a powder dispersion comprising:
from 0.1% to 99.9% by weight, preferably from 0.1% to 30% by weight, of powder particles in accordance with the invention,
from 0.1% to 99.9% by weight, preferably from 70% to 99.9% by weight, of solvent in accordance with the invention, relative to the total weight of the dispersion.

The invention can also be included in a cosmetic and/or perfumery composition. Advantageously, said cosmetic and/or perfumery composition comprises:
from 0.1% to 99.9%, preferably from 0.1% to 30% by weight, of powder particles according to the invention,
from 0.1% to 99.9%, preferably from 70% to 99.9% by weight, of a medium that is acceptable in cosmetics and/or in perfumery, relative to the total weight of the composition.

Advantageously, said composition is a colored, noncolored or transparent product chosen from the following products:
makeup products for the human face and body, such as a foundation, tinted cream, loose or compact powder, eyeshadow, mascara, eyeliner or lipstick,
care products for the human face and body, such as a cream, milk, lotion, mask, exfoliation product, cleansing and/or makeup-removal products, deodorants, antiperspirants, shaving products or hair-removal products,
hair products, such as shampoos, hair shaping products, hairstyle maintaining products, antidandruff products, anti-hair loss products, products to counteract dryness of the hair, hair dyes or bleaching products,
perfumery products, such as a fragrance, milk, cream or loose or compact powder which is fragranced.

Since ester chemistry is experiencing a growing development, an increasing number of commercial products are proposed, increasing the advantage of the present invention.

Another advantage of the present invention is that of carrying out the synthesis of polyamide powder at temperatures below that of the prior art. This results in energy savings and a positive impact on the environment.

The present invention makes it possible to overcome several drawbacks of the prior art. It more particularly provides a process for producing polyamide from at least one diester and at least one diamine and/or at least one amino ester, in which the polyamide powder obtained has advantageous characteristics and is notably easy to synthesize. The process makes it possible to carry out, at low temperature (temperature below 200° C.) and in a dispersed medium, the production of polyamide powder having a controlled particle size, a spheroidal morphology and a surface porosity.

This type of reaction for a diamine/diacid pair cannot be carried out by those skilled in the art under these conditions because of the non-reactivity of the diamine/diacid pair under the conditions specific to the precipitation polymerization process. The applicant has discovered that, surprisingly, the precipitation polymerization process can be used according to the invention, by virtue of the reactivity of diesters with diamines. Indeed, the ester aminolysis reaction makes it possible to use a precipitation polymerization process normally reserved for the anionic polymerization of lactams in solution. The polycondensation of at least one diester and at least one diamine and/or at least one amino ester gives excellent results in a reaction carried out according to the invention. It is advantageous to note that the presence of an initiator and of an activator usually required in such reactions is not required in the present invention. Advantageously, the reaction according to the invention is thus carded out much more simply than with lactams, in temperature ranges around 100° C. and with stirring.

DESCRIPTION OF EMBODIMENTS OF THE INVENTION

The invention is now described in greater detail and in a nonlimiting manner in the description which follows.

Unless otherwise indicated, the proportions or percentages indicated are by weight.

For the purposes of the invention, the term "polycondensate" is intended to mean both an oligomer and/or a polyamide obtained by polycondensation.

For the purposes of the invention, the term "polyamide" is intended to mean the products of condensation of amino esters and/or diesters with diamines and, as a general rule, any polymer formed by units linked to one another by amide groups.

For the purposes of the invention, the term "oligomer" is intended to mean a chemical molecule consisting of one to four monomers.

For the purposes of the invention, the term "monomer" is intended to mean a repeating unit of the oligomer or of the polyamide. The case where a repeating unit consists of the combination of a diester with a diamine is particular. It is considered that it is the combination of a diamine and of a diester, that is to say the diamine.diester pair (in equimolar amount), which corresponds to the monomer. This is explained by the fact that, individually, the diester or the diamine is just one structural unit, which is not sufficient on its own to form a polymer.

The invention envisions producing a polycondensate powder from at least one diester and at least one diamine, and/or at least one amino ester, as defined above.

According to one particular embodiment of the invention, a single diamine diester pair is used, so as to form a homopolyamide.

According to one preferred embodiment of the invention, two or more diamine diester pairs are used, so as to form a copolyamide (CoPA).

According to another particular embodiment, a single amino ester having a single index n is used so as to form a homopolyamide.

According to an even more preferred embodiment, two or more amino esters having different indices n are used, so as to form a CoPA.

According to the process of the invention, introduced for example into a reactor are the monomer(s) included in the range of from 20% to 75%, preferably 30%, by weight of at least one diester and at least one diamine and/or of at least one amino ester, in a dispersion solvent, relative to the total weight of dispersion. The solvent may comprise in particular one or more of the following compounds: linear alkanes, cycloaliphatic alkanes, halogenated solvents and mixtures thereof. The solvent preferably comprises a solvent of Shellsol type. The term "solvent of Shellsol type" is intended to mean a solvent consisting of a hydrocarbon fraction.

It is also possible to introduce into the medium a polycondensation catalyst, the content of which is included in the range of from 0 to 50 mol %, preferably from 0.01 mol % to 50 mol %, preferably from 0.01 mol % to 30 mol %, preferably from 0.01 mol % to 20 mol %, relative to the number of moles of all of the reagents. The use of a catalyst has an advantageous effect on the control of the polymerization and on the precipitation of the powders. According to one advantageous embodiment of the process of the invention, an acid catalysis and a basic catalysis can alternatively be used. Preferably, a basic catalysis, preferably comprising sodium methoxide, is used.

The reaction temperature is included in the range of from 30° C. to the boiling point of the solvent, preferably from 50° C. to 120° C., preferably from 80° C. to 110° C., preferably equal to 100° C.

Stirring is applied to the reaction medium, preferably included in the range of from 1 to 2000 rpm, preferably 150 rpm, preferably 310 rpm. This stirring can be carried out by any system sufficient to bring about the dispersion of the PA powders in the solvent, including by shear.

According to one advantageous embodiment of the invention, the stirring is carried out by means of a paddle stirring system, preferably by means of a paddle and counter-paddle stirring system.

This step lasts for example at least one hour, or at least two hours, or at least three hours, or at least four hours, or at least five hours.

The temperature is preferably constant. Alternatively, this temperature can vary for example in a monotone or cyclic manner or in steps. A temperature increase phase can be provided for at the beginning of the process or before. Preferably, said phase lasts less than 30 minutes, or less than 20 minutes, or less than 15 minutes, or less than 10 minutes.

The ester aminolysis results, according to the process of the invention, in the formation of a polycondensate. According to the invention, the ester aminolysis, by reaction of at least one diamine and at least one diester and/or of at least one amino ester, leads directly to the synthesis of polycondensate.

Parasitic reactions can theoretically be observed, such as a cyclization of the diester, an intramolecular cyclization, an intermolecular cyclization or an N,N'-dimethylation. The alkylation of the amines by the esters, originating from the competition of the acyl-alkyl groups (N-alkylation), leads to the interruption of the formation of the polyamide, since there is permanent formation of nonreactive chain ends. Without being bound by any theory, the inventors think that, by virtue of the process according to the invention, only the last reaction is possible at low temperature (temperature below 200° C.), all the other reactions being linked to a high temperature (greater than or equal to 200° C.). The lower the reaction temperature, the less the N-alkylation occurs. Advantageously, the process according to the invention makes it possible to reduce or even prevent the parasitic reactions.

Simultaneously with the polycondensation, a dispersion of powder in the solvent forms. The reaction medium opacifies, marking the start of the formation of a powder, preferably after one hour.

The powder dispersion can be stored in this state or else the powder can be separated from the dispersion solvent and recovered. Preferably, the polycondensate is thus recovered in powder form.

Where appropriate, the separation step can be carried out according to any liquid-solid separation techniques, preferably by solvent evaporation.

Various additives can also be introduced into the medium, in particular organic fillers, such as PA, or mineral fillers, such as silica; and/or surfactants.

Advantageously, an organic or mineral filler, preferably silica, is added to the reaction medium to assist with the precipitation by making it possible to control the size distribution of the particles. Use may be made of a 5 μm hydrophilic silica (Sipernat 320DS), but use is preferably made of a hydrophobic silica consisting of agglomerates which are smaller than one micrometer in size (Aerosil R972). The addition of silica has an advantageous effect on the size of the polycondensate powder. In the absence of such a filler, the powder tends to form agglomerates which coalesce, and in this case it proves to be difficult, or even impossible, to control the size distribution of the particles, and thus to obtain a powder with a D50 of less than 100 μm, or even a D50 of less than 200 μm.

Advantageously, various types of surfactants can be added to the reaction medium. These surfactants make it possible to stabilize the growing particles in the reaction medium. They may for example be sodium stearate or butanol, preferably butanol.

The number-average molar mass of the polyamide obtained can be determined by size exclusion chromatography, using hexafluoroisopropanol (HFIP) as solvent and eluent, and a refractometric detection. The number-average molar mass of the polyamide obtained can also be determined by NMR (nuclear magnetic resonance), or else by quantitative determination of the chain ends. NMR is preferably used to determine the number-average molar mass.

The characteristics of the powders of polyamide, which is the subject of the invention, are in particular:
- the mean particle diameter of from 1 to 200 μm, preferably from 1 to 100 μm, even more advantageously from 5 to 60 μm;
- the narrow particle size distribution by volume. The particle size distribution by volume of the powders is determined according to the usual techniques, for example using a Coulter LS 230 particle size analyzer, according to ISO standard 13320-1:1999. On the basis of the particle size distribution by volume, it is possible to determine the volume mean diameter ("D50") and also the particle size dispersion (standard deviation) which measures the width of the distribution. It is one of the advantages of the process described that it makes it possible to obtain a tight or narrow (dispersion) particle size distribution by volume;
- the spheroidal shape of the particles, that is to say in the shape of a spheroid, which has a shape similar to that of a sphere;
- the particle surface porosity, measured by the apparent specific surface area (also called SSA). The particles of the invention have an SSA measured according to the BET method ranging from 1 to 20 $m^2/g$, preferably from 2 to 10 $m^2/g$, preferably from 3 to 6 $m^2/g$. The BET (Brunauer-Emmet-Teller) method is a method known to those skilled in the art. It is in particular described in *The journal of the American Chemical Society*, vol. 60, page 309, February 1938, and corresponds to international standard ISO 5794/1. The specific surface area measured according to the BET method corresponds to the total specific surface area, that is to say that it includes the surface area formed by the pores.

EXAMPLES

The following examples illustrate the invention without limiting it.

Example 1—Precipitation Polymerization of a PA 6.10

A dibutyl sebacate/hexamethylenediamine reaction mixture is prepared in a 1:1 weight ratio. The reaction mixture is introduced into a glass reactor in an amount of 30% by weight in Shellsol. Sodium methanolate is added to the reaction medium in an amount of 17 mol % relative to one of the monomers. The reaction is carried out with stirring at 150 rpm and heated up to a temperature of 100° C. The reaction time is 7 hours.

The medium is then filtered so as to recover the PA 6.10 powder, and then the powder is washed with ethanol, and then with water and finally oven-dried at 75° C.

The powder is analyzed by $^1H$ NMR and DSC.

The total yield by weight is 72%. This yield by weight is calculated by calculating the ratio of the weight of powder obtained after washing and drying to the weight of powder theoretically expected at the end of reaction.

The PA 6.10 powder obtained has a molar mass of approximately 1200 g/mol.

The PA 6.10 powder obtained has a melting point ($M_p$) equal to 201° C. and a viscosity of 0.23 (according to Arkema method: 0.5 g/dl in metacresol at 25° C.).

The D50 of the powder is then measured according to ISO standard 13320-1:1999. The mean diameter of the powder particles obtained is 80 μm.

TABLE 1

| $^1H$ NMR analysis of example 1 | |
|---|---|
| Molar ratio | Ex. 1 |
| Secondary amide | 76.12% |
| Ester | 3.79% |
| Acid | 5.76% |
| Primary amine | 11.60% |
| Alcohol | 2.72% |

The NMR analyses clearly show the production of a polyamide from a diester and from a diamine.

Tests: Influence of the Catalyst Concentration and of the Temperature Profile on the Synthesis Yield by Weight Tests were carried out by varying the catalyst concentration. The conditions used are identical to those of example 1. The results are presented in the following table (the higher the yield by weight, the more efficient the reaction).

TABLE 2

Influence of the catalyst concentration on the yield

| Test | Catalyst [mol %] | Yield by weight |
|---|---|---|
| 1 | 17 | 72% |
| 2 | 9 | 20% |
| 3 | 40 | 72% |

According to the yields by weight obtained under the conditions of example 1, it is possible to conclude that there is an optimal loading of sodium methanolate (reaction catalyst): approximately 17 mol %. Indeed, with less catalyst (9 mol %), the reaction gives a lower yield by weight; and with more catalyst (40 mol %), there is no improvement observed compared to 17 mol %.

Tests were carried out by varying the reaction temperature. The results are presented in the following table (the higher the yield by weight, the more efficient the reaction).

TABLE 3

Influence of the thermal profile on the action of the sodium methanolate

| Test | Catalyst [%] | Thermal profile | Precipitation yield by weight |
|---|---|---|---|
| 1 | 17 | 100° C. over the course of 7 h | 72% |
| 4 | 17 | 100° C. over the course of 15 h | 72% |
| 5 | 17 | 80° C. over the course of 15 h | 52% |
| 6 | 17 | 120° C. over the course of 7 h | 13% |

According to the yields by weight obtained, it is possible to conclude that there is an optimal synthesis temperature: 100° C. Indeed, it appears that, with a lower temperature (80° C.) or a higher temperature (120° C.), the reaction is less efficient.

Tests were carried out by varying the stirring speed of the reaction medium. The results are presented in the following table (the higher the yield by weight, the more efficient the reaction).

TABLE 4

Influence of the stirring speed on the particle size

| Test | Stirring speed [rpm] | Mean diameter [μm] |
|---|---|---|
| 1 | 150 | 100 |
| 7 | 310 | 80 |

The stirring speed has a direct effect on the size of the polycondensate powder particles; the faster the stirring, the smaller the particles.

Example 2—Oil/Water Emulsion of the Polycondensate Powder According to the Invention A formulation A for a cosmetic cream, of the oil-in-water type, having the following composition by weight is prepared:
Water 83.44%.
Chlorphenesin: 0.28%.
Xanthan gum: 0.2%.
Hydroxyethyl acrylate and copolymer of sodium acryloyldimethyl taurate: 0.5%.
Arachidyl alcohol and behenyl alcohol and arachidyl glucoside: 3.0%.
Caprylic/capric triglycerides: 5.0%.
Cyclohexasiloxane: 1.0%.
Phenoxyethanol and ethylhexylglycerol: 0.5%.
Antioxidant: 0.08%.
Glycerol: 3.0%.
Composition according to the invention: 3.0%.

A formulation B for a pressed cosmetic powder for smoothing out imperfections, having the following composition by weight, is prepared:
Octyldodecyl xyloside: 5.0%.
Isostearyl isostearate: 3.0%.
Talc: 44.7%.
Mica: 30.0%.
Talc and disodium stearoyl glutamate/aluminum hydroxide: 5.0%.
Cellulose: 5.0%.
Salicylic acid: 0.2%.
Pigments: 2.1%.
Composition according to the invention: 5.0%.

In the two formulations above, the composition according to the invention is produced from particles of copolyamide 6112.

The particles have a volume-mean diameter D50 of 10 μm.

The composition has a pH included in the range of from 5 to 9, for example of 7.5.

The invention claimed is:

1. A process for producing a polycondensate powder dispersion, wherein the process comprises polycondensation:
  i) of at least one diester and at least one diamine, and/or
  ii) of at least one amino ester,
  with stirring, in a solvent that can dissolve both the diamine and the diester and/or the amino ester, but not a polyamide which forms during the polycondensation, at a temperature included in the range of from 50° C. to 120° C. such that a polycondensate powder precipitate dispersed in the solvent is obtained,
  wherein the process further comprises a step of separation of the solvent and recovering a polycondensate powder, wherein the polycondensate powder comprises particles of free powder which have a spheroidal shape, a D50 measured according to ISO standard 13320-1: 1999 included in the range of from 1 to 200 μm, and which comprise traces of ester chain ends,
  wherein said at least one diester is of formula:
  $R_1$—$(CH_2)_m$—$R_2$, wherein m represents an integer ranging from 0 to 36, and $R_1$ and $R_2$ represent identical or different ester functions of general formula $COOR_3$, wherein $R_3$ represents a saturated or unsaturated, linear or branched alkyl chain of from 1 to 5 carbon atoms and/or $R_1$—$(C_6H_4)_n$—$R_2$, wherein n represents an integer ranging from 1 to 2, and $R_1$ and $R_2$ represent identical or different ester functions of general formula COOR$_3$, wherein R$_3$ represents a saturated or unsaturated, linear or branched alkyl chain of from 1 to 5 carbon atoms;

wherein said at least one diamine is chosen from aliphatic diamines having from 6 to 12 carbon atoms;

wherein said at least one amino ester corresponds to the general formula R$_5$—(CH$_2$)$_p$—R$_6$, wherein p represents an integer ranging from 0 to 36, R$_5$ represents a primary or secondary amine function, and R$_6$ represents an ester function of general formula COOR$_7$, wherein R$_7$ represents an alkyl chain of from 1 to 5 carbon atoms;

wherein the solvent is chosen from linear alkanes, cycloaliphatic alkanes, halogenated solvents and mixtures thereof.

2. The process as claimed in claim 1, wherein said polycondensation is carried out in the presence of a polycondensation catalyst, the content of which is included in the range of from 0.01 mol % to 50 mol %, relative to the number of moles of all of the reagents, wherein the polycondensation catalyst is chosen from sodium hydride, potassium hydride, sodium, sodium stearate, ortho-phosphoric acid, stearic acid, ethanol, phenol, sodium methoxide, sodium ethoxide, and mixtures thereof.

3. The process as claimed in claim 1, wherein the polycondensation comprises a simultaneous precipitation in the form of polycondensate powders.

4. The process as claimed in claim 1, wherein the stirring is at a speed included in the range of from 1 to 2000 rpm.

5. The process as claimed in claim 1, wherein the process comprises at least one step of polycondensation of at least one diester and at least one diamines.

6. The process as claimed in claim 1, wherein the process comprises at least one step of polycondensation of at least one amino ester.

7. The process as claimed in claim 1, wherein the particles of free powder comprise 10 to 4000 meq/kg of ester chain ends, relative to the weight of polycondensate.

8. The process as claimed in claim 1, wherein the process comprises at least one step of polycondensation at a temperature in the range of 50° C. to 120° C.

* * * * *